United States Patent
Rong

(10) Patent No.: US 10,259,777 B2
(45) Date of Patent: Apr. 16, 2019

(54) (E)-3-(3,4-DIHYDROXYPHENYL)-N-(PROP-2-YN-1-YL)ACRYLAMIDE FOR TREATMENT OF NEURODEGENERATIVE DISEASES

(71) Applicant: THE UNIVERSITY OF HONG KONG, Hong Kong (CN)

(72) Inventor: Jianhui Rong, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 0 days.

(21) Appl. No.: 15/578,120

(22) PCT Filed: May 13, 2016

(86) PCT No.: PCT/CN2016/082007
§ 371 (c)(1),
(2) Date: Nov. 29, 2017

(87) PCT Pub. No.: WO2016/192525
PCT Pub. Date: Dec. 9, 2016

(65) Prior Publication Data
US 2018/0155275 A1 Jun. 7, 2018

Related U.S. Application Data

(60) Provisional application No. 62/168,023, filed on May 29, 2015.

(51) Int. Cl.
| C07C 235/34 | (2006.01) |
| A61P 25/28 | (2006.01) |
| A61P 25/16 | (2006.01) |
| C07C 231/10 | (2006.01) |
| C07C 231/24 | (2006.01) |
| A61K 38/18 | (2006.01) |

(52) U.S. Cl.
CPC .......... *C07C 235/34* (2013.01); *A61K 38/185* (2013.01); *A61P 25/16* (2018.01); *A61P 25/28* (2018.01); *C07C 231/10* (2013.01); *C07C 231/24* (2013.01)

(58) Field of Classification Search
CPC .................................................. A61K 31/165
USPC ........................................ 514/622; 564/204
See application file for complete search history.

(56) References Cited

PUBLICATIONS

Healy, Daniel G. et al., Phenotype, Genotype, and worldwide genetic penetrance of LRRK2-associated Parkinson's disease: a case-control study, Lancet Neurology, Jul. 2008, 7(7):583-590, Elsevier Inc.
Perfeito, Rita et al., Revisiting oxidative stress and mitochondrial dysfunction in the pathogenesis of Parkinson disease-resemblance to the effect of amphetamine drugs of abuse, Free Radical Biology and Medicine, Nov. 2012, 53(9):1791-1806, Elsevier Inc.
Bonuccelli, Ubaldo et al., New pharmacologic horizons in the treatment of Parkinson disease, Neurology, Oct. 2006, 67(2):S30-S38, AAN Enterprises, Inc.
Müller, Thomas, Non-dopaminergic drug treatment of Parkinson's disease, Expert Opinion on Pharmacotherapy, 2001, 2(4):557-572, Ashley Publications Ltd.
Meissner, Wassilios G. et al., Priorities in Parkinson's disease research, Nature Reviews Drug Discovery, May 2011, 10(5):377-393, Macmillan Publishers Limited.
Marxreiter, Franz et al., Adult neurogenesis in Parkinson's disease, Cellular and Molecular Life Sciences, 2013, 70(3):459-473, Springer Basel AG 2012.
Lamm, Omri et al., Harnessing Neurogenesis for the Possible Treatment of Parkinson's Disease, The Journal of Comparative Neurology, Aug. 2014, 522(12):2817-2830, Wiley Periodicals, Inc.
Rangasamy, Suresh Babu et al., Neurotrophic factor therapy for Parkinson's disease, Progress in Brain Research, 2010, 184:237-264, Elsevier B.V.
Sullivan, Aideen M. et al., Neurotrophic factors for the treatment of Parkinson's disease, Cytokine & Growth Factors Reviews, Jun. 2011, 22(3):157-65, Elsevier Ltd.
Ma, Qiang, Role of Nrf2 in Oxidative Stress and Toxicity, The Annual Review of Pharmacology and Toxicology, 2013, 53:401-426, Annual Reviews.

(Continued)

*Primary Examiner* — Douglas M Willis
(74) *Attorney, Agent, or Firm* — Saliwanchik, Lloyd & Eisenschenk

(57) ABSTRACT

The present invention pertains to a pharmaceutical composition comprising a pharmaceutically acceptable carrier and (E)-3-(3,4-dihydroxyphenyl)-N-(prop-2-yn-1-yl)acrylamide of Formula (I):

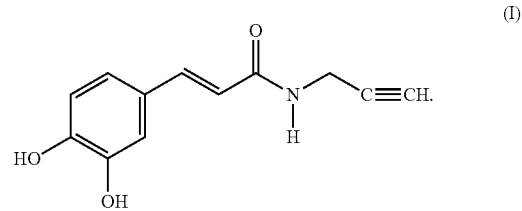

The invention also pertains to a method for stimulating neurite outgrowth by administering to cells in the area where neurite outgrowth is desired a therapeutically effective amount of the compound of Formula (I). Further, the invention pertains to a method for attenuating neuron injury in a subject by contacting a neuron in a subject in need thereof with a therapeutically effective amount of the compound of Formula (I). Furthermore, a method of preparing the compound of Formula (I) are provided.

14 Claims, 11 Drawing Sheets

(56) References Cited

PUBLICATIONS

Joshi, Gururaj et al., The Nrf2-ARE pathway: a valuable therapeutic target for the treatment of neurodegenerative diseases, Recent Pat CNS Drug Discovery, Dec. 2012, 7(3):218-229.

Satoh, Takumi et al., Nrf2/ARE-mediated antioxidant actions of pro-electrophilic drugs, Free Radical Biology and Medicine, Dec. 2013, 65:645-657, Elsevier Inc.

Zhang, Donna D. et al., Distinct Cysteine Residue in Keap1 Are Required for Keap1-Dependent Ubiquitination of Nrf2 and for Stabilization of Nrf2 by Chemopreventive Agents and Oxidative Stress, Molecular and Cellular Biology, Nov. 2003, 23(22):8137-8151, American Society for Micrbiology.

Paine, Ananta et al., Signaling to heme oxygenase-1 and its anti-inflammatory therapeutic potential, Biochemical Pharmacology, Dec. 2010, 80(12):1895-1903, Elsevier Inc.

Gozzelino, Raffaella et al., Mechanisms of Cell Protection by Herne Oxygenase-1, The Annual Review of Pharmacology and Toxicology, Feb. 2010, 50:323-354, Annual Reviews.

Kärkkäinen, Virve et al., Nrf2 Regulates Neurogenesis and Protects Neural Progenitor Cells Against Aβ Toxicity, Stem Cells, 2014, 32(7):1904-1916, AlphaMed Press.

Zhao, Fei et al., Nrf2 promotes neuronal cell differentiation, Free Radical Biology & Medicine, Sep. 2009, 47(6):867-879, Elsevier Inc.

Kumar, Hemant et al., Nuclear Factor Erythroid 2—Related Factor 2 Signaling in Parkinson Disease: A Promising Multi Therapeutic Target Against Oxidative Stress, Neuroinflammation and Cell Death, CNS & Neurological Disorders—Drug Targets, 2012, 11(8):1015-1029, Bentham Science Publishers.

Chen, Liang-Wei et al., Chinese Herbs and Herbal Extracts for Neuroprotection of Dopaminergic Neurons and Potential Therapeutic Treatment of Parkinson's Disease, CNS & Neurological Disorders—Drug Targets, 2007, 7(6):273-281, Bentham Science Publishers Ltd.

Campos, Helineide Cristina et al., The Role of Natural Products in the Discovery of New Drug Candidates for the Treatment of Neurodegenerative Disorders I: Parkinson's Disease, CNS & Neurological Disorders—Drug Targets, 2011, 10(2):239-250, Bentham Science Publishers.

Da Cunha, Fernanda M. et al., Caffeic Acid Derivatives: in Vitro and in Vivo Anti-inflammatory Properties, Free Radical Research, Nov. 2004, 38(11):1241-1253, Taylor & Francis Ltd.

Fiuza, S. M. et al., Phenolic acid derivatives with potential anticancer properties—a structure-activity relationship study. Part 1: Methyl, propyl and octyl esters of caffeic and gallic acids, Bioorganic & Medicinal Chemistry, 2004, 12(13):3581-3589, Elsevier Ltd.

Yang, Chuanbin et al. Biochemical mechanisms of bornyl caffeate induced cytotoxicity in rat pheochromocytoma PC12 cells, Chemico-Biological Interactions, 2014, 219:133-142, Elsevier Ireland Ltd.

Yang, Chuan-Bin et al., Bornyl caffeate induces apoptosis in human breast cancer MCF-7 cells via the ROS- and JNK-mediated pathways, Acta Pharmacologica Sinica, 2013, 1-11, 2013 CPS and SIMM.

Kurauchi, Y et al., Caffeic acid phenethyl ester protects nigral dopaminergic neurons via dual mechanisms involving haem oxygenase-1 and brain-derived neurotrophic factor, British Journal of Pharmacology, 2012, 166(3):1151-1168, The Authors British Journal of Pharmacology and The British Pharmacological Society.

Wei, Xing et al., Caffeic acid phenethyl ester prevents neonatal hypoxic-ischaemic brain injury, Brain, Oct. 2004, 127(12):2629-2635, Guarantors of Brain 2004.

Deguire, Sean M. et al., Fluorescent Probes of the Apoptolidins and their Utility in Cellular Localization Studies, Angewandte Chem., 2015, 127:975-978, Wiley-VCH Verlag GmbH & Co. KGaA, Weinheim.

International Search Report in International Application No. PCT/CN2016/082007, filed May 13, 2016.

Jiaranaikulwanitch, Jutamas et al., From BACE1 Inhibitor to Multifunctionality of Tryptoline and Tryptamine Triazole Derivatives for Alzheimer's Disease, Molecules, 2012, 17:8312-8333, doi: 10.3390/molecules17078312.

1) NGF; 2) NGF+PACA; 3) NGF+Caffeic acid; 4) NGF+CAPE

(E)-3-(3,4-DIHYDROXYPHENYL)-N-(PROP-2-YN-1-YL)ACRYLAMIDE FOR TREATMENT OF NEURODEGENERATIVE DISEASES

CROSS-REFERENCE TO RELATED APPLICATIONS

This application is the U.S. national stage application of International Patent Application No. PCT/CN2016/082007, filed May 13, 2016, which claims the benefit of U.S. Provisional Application Ser. No. 62/168,023, filed May 29, 2015, the disclosures of each of which are incorporated herein by reference in their entirety.

BACKGROUND OF THE INVENTION

Parkinson's disease (PD) is the second most common neurodegenerative disease and affects 1-2% elderly people above the age of 65 while one-tenth of patients are diagnosed at the age around 50 worldwide[1]. The etiology of PD is still not clear, but it's believed that oxidative injury causes the loss of dopamine-secreting neurons in substantia nigra, and subsequent symptoms including tremor, stiffness and movement disorders[2]. L-DOPA, dopamine agonists, MAO-B inhibitors and NMDA receptor antagonists have been recently evaluated to ameliorate the motor symptoms in PD patients[3,4]. None of the current therapies is clinically proven for halting progression of neurodegeneration[5]. On the other hand, neurogenesis is often impaired in aging brains, PD and other neurodegenerative disorders due to the insufficient production of neurotrophic factors[6]. Interestingly, neurogenesis is also reduced in 6-hydroxydopamine (6-OHDA)-induced PD animal models and transgenic mice that overproduce human α-synuclein[7]. In fact, neurotrophic factor therapies have been evaluated to enhance neurogenesis for the treatment of PD and Alzheimer's disease[8]. However, the clinical applications of NGF and several other neurotrophic factors have been dampened by the delivery issues and side effects[9]. Thus, enormous effort has been made to search for small molecules to mimic or enhance the pharmacological effects of neurotrophic factors on neuroprotection and neuroregeneration.

Nuclear factor erythroid 2-related factor 2 (Nrf2) is an important intracellular redox-sensitive transcription factor[10,11]. The Keap1-Nrf2-ARE pathway regulates the cellular defense mechanisms against oxidative stress. The Keap1-Nrf2-ARE pathway has become an attractive target for the prevention and treatment of oxidative stress-related diseases including cancer, neurodegenerative, cardiovascular, metabolic, and inflammatory diseases. Importantly, various electrophilic inducers disassociate the Nrf2-Keap1 complex via covalently modifying Keap1[12,13]. Consequently, Nrf2 is translocated into the cell nucleus and activates the expression of various phase II defense enzymes, antioxidant proteins and anti-inflammatory factors[10,11]. As an example, heme oxygenase-1 (HO-1) is induced by Nrf2-mediated mechanism. HO-1 catalyzes the degradation of pro-oxidant heme to biliverdin/bilirubin, carbon monoxide and ferrous ion. HO-1 thereby exhibits a broad range of biological activities such as antioxidant, anti-inflammatory, neuroprotective and immunomodulatory activities[14,15]. Importantly, the Nrf2/HO-1 pathway also plays a key role in neurogenesis and neurite outgrowth[16,17]. Therefore, the Nrf2/HO-1 pathway becomes a therapeutic target in the treatment of various neurodegenerative disorders including PD[12,15,18].

Natural products constitute a rich resource for the identification of neuroprotectants and neuroregenerative reagents[19,20]. Caffeic acid derivatives exert anti-oxidant, anti-inflammatory, chemopreventive, anticancer and antibacterial properties in a structure-dependent and cell-type-specific manner[21,22]. It has recently been demonstrated that bornyl caffeate induced apoptosis in several cancer cell lines via stimulating GSH depletion, ROS formation and mitochondrial dysfunction[23,24]. Nevertheless, recent studies also demonstrated that caffeic acid derivatives induced brain-derived neurotrophic factor (BDNF) expression and scavenged neurotoxic peroxynitrite[25,26]. However, caffeic acid derivatives have not been investigated for neuroprotection and neuritogenesis against 6-OHDA induced neurotoxicity.

BRIEF SUMMARY OF THE INVENTION

The present invention is directed to compounds, pharmaceutical compositions, and related methods of treatment and/or prevention for neurodegenerative diseases.

Aspects of the present invention provide a compound of formula (1):

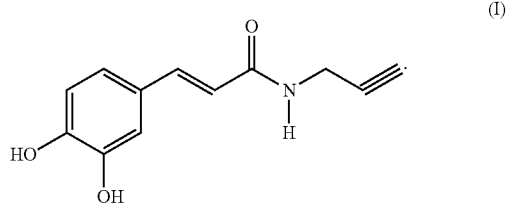 [SMILES: C#CCNC(=O)/C=C/c1ccc(O)c(O)c1]

Aspects of the present invention also provide pharmaceutical compositions comprising the compound of formula (I) and a pharmaceutically acceptable carrier.

Aspects of the present invention further provide methods of treating or preventing a neurodegenerative disease in a subject, comprising administering an effective amount of the compound of formula (I) to a subject in need thereof. In some embodiments, the neurodegenerative disease is Parkinson's disease.

Aspects of the present invention provide methods of stimulating neurite outgrowth in an area where neurite outgrowth is desired, the methods comprising administering an effective amount of a compound of formula (I) to cells in the area where neurite outgrowth is desired, whereby neurite outgrowth is stimulated. In some embodiments, the methods further comprise administering an effective amount of a nerve growth factor.

Aspects of the present invention also provide methods of attenuating neuron injury, comprising contacting neurons, in need thereof, with an effective amount of a compound of formula (I), whereby neuron injury is attenuated in a heme oxygenase-1 dependent manner.

DETAILED DESCRIPTION OF THE INVENTION

Figure 1:
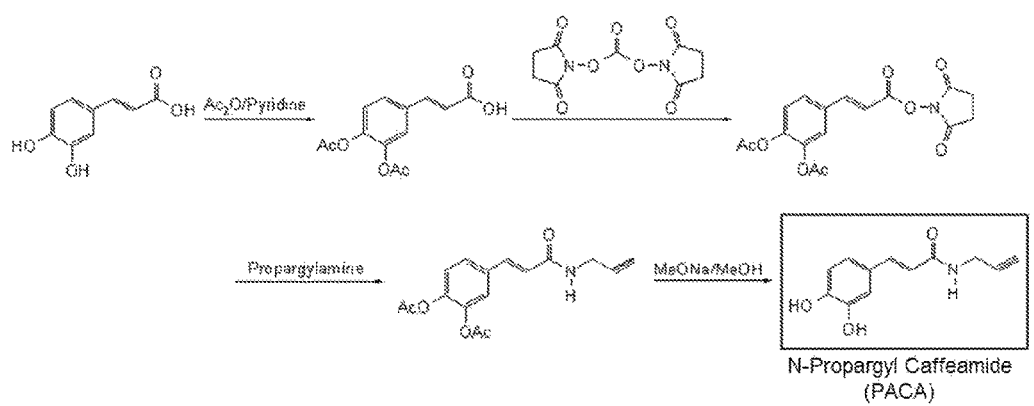
FIG. 1 illustrates a synthetic scheme for the preparation of N-propargyl caffeamide (PACA). PACA was synthesized from caffeic acid and propargylamine through four steps including acetylation, activation of carboxylic acid group, amination and deacetylation. The overall yield was 65%. Ac$_2$O, acetic anhydride; MeONa, sodium methoxide; MeOH, methanol.
Figure 2:
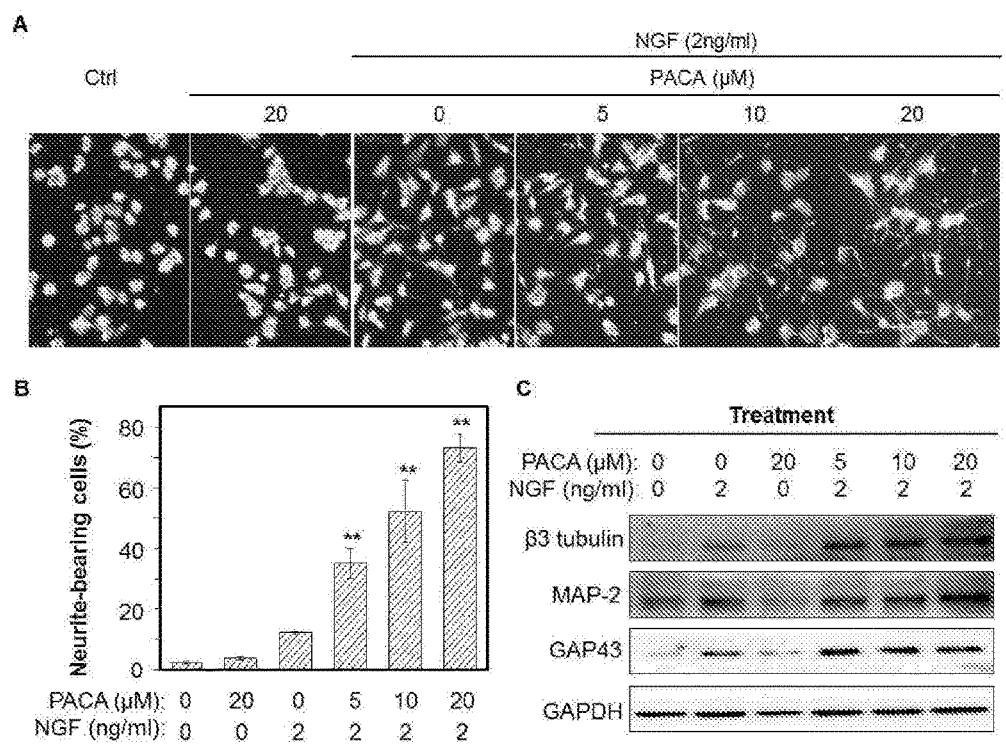
FIG. 2 shows that PACA enhances NGF-induced neuritogenesis in PC12 cells. PACA effectively enhanced nerve growth factor (NGF)-induced neuritogenesis in rat pheochromocytoma PC12 cells line in a concentration-dependent manner. The neuritogenic potential of PACA was verified by the induction of the main neuronal biomarkers (i.e., β3-tubulin, MAP-2 and GAP43). (A) Representative images for the potentiation of NGF-induced neurite outgrowth in PC12 cells by PACA. PC12 cells were treated with NGF (2 ng/ml) and PACA, alone or in combination. The cells were stained with neurite outgrowth staining kit and imaged under a fluorescence microscope. (B) Quantification of neurite outgrowth in Panel A. Following the staining of neurites, the cells bearing neurites longer than 20 μm were counted under a fluorescence microscope. **, p<0.01 (sample vs NGF alone). (C) Western blot analysis of neuronal biomarkers. The cells were treated with NGF and PACA, alone or in combination, whereas the control cells were treated with vehicle for 72 hours. The cellular proteins were extracted and detected by Western blot analysis for the expression of neuron marker. GAPDH was detected as the control of protein loading.
Figure 3:
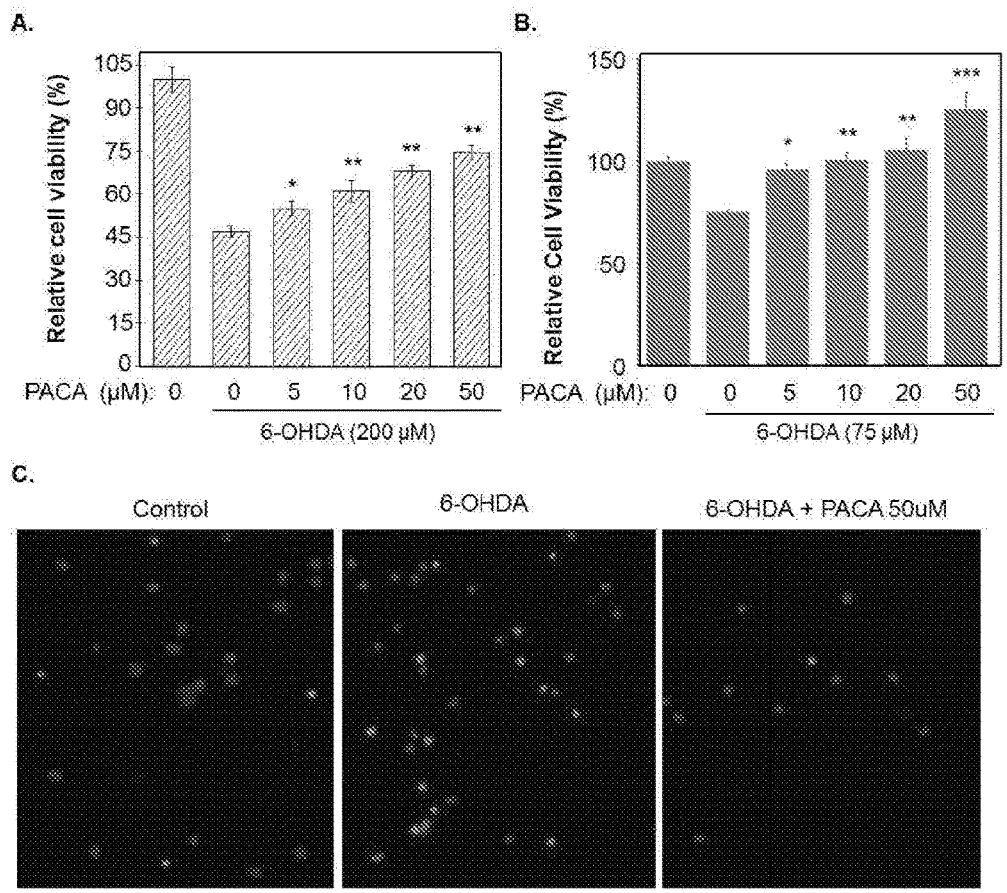
FIG. 3 shows the neuroprotective effect of PACA against 6-OHDA-induced neuronal death. Neurotoxin 6-hydroxydopamine (6-OHDA) is widely used to induce the cell model of human Parkinsonism. PC12 cells were treated with 6-OHDA with or without PACA for 24-hours, the cell viability was assessed by the colorimetric MTT assay. The relative cell viability was plotted against the concentrations of PACA. On the other hand, primary midbrain neurons were isolated from 17-day-old Sprague Dawley (SD) rat embryos. The midbrain neurons were treated with 6-OHDA with or without PACA for 12-hours, the cell viability was assessed by the colorimetric MTT assay. Alternatively, the neurons were stained with 5 μM of Hoechst 33342 and 1 μM of PI in the differentiation medium at 37° C. for 30 min. The images were captured on a Zeiss fluorescence microscope. (A) MTT assay of the cell viability in PC 12 cells. PC12 cells were treated with 6-OHDA alone or in combination with PACA for 24 h. The cell viability was examined by standard MTT assay. The values represent means±SD (n=3). *, p<0.05; **, p<0.01 (6-OHDA+PACA vs 6-OHDA alone). (B) MTT assay of the neuronal viability in rat midbrain neurons. Primary rat embryonic midbrain neurons were treated with 6-OHDA alone or in combination with PACA for 24 h. The neuronal viability was examined by standard MTT assay. The values represent means±SD (n=3). *, p<0.05; , p<0.01; *, p<0.001 (6-OHDA+PACA vs 6-OHDA alone). (C) Hoechst 33342/PI staining of 6-OHDA-induced apoptosis in rat midbrain neurons. Primary rat embryonic midbrain neurons were treated with 6-OHDA alone or in combination with PACA for 24 hours. The neurons were incubated with PI/Hoechst 33342. PI-positive and Hoechst 33342-stained neurons were counted under a fluorescence microscope. Representative images from two independent experiments were shown.
Figure 4:
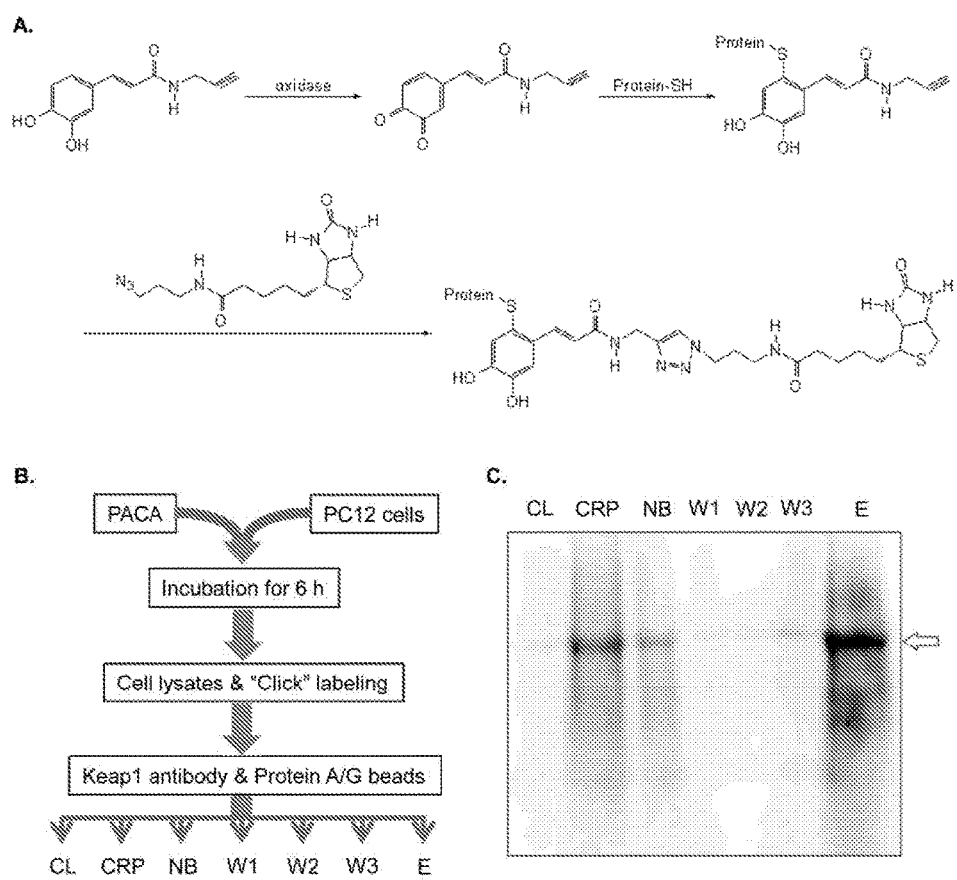
FIG. 4 shows identification of PACA-modified proteins after click-chemistry tagging of biotin and affinity isolation. PACA directly modifies the proteins bearing free cysteine residues after oxidase-mediated oxidation into chemically reactive o-quinone. At the end of 24 hour incubation, a biotin tag was introduced to the proteins that were covalently modified by PACA. Following affinity isolation with anti-Keap1 antibody bead, streptavidin-horseradish peroxidase (HRP) detected Keap1 as the predominant PACA-modified protein with the apparent molecular size of ~72 kDa. (A) Biotinylation of PACA-modified proteins by Click chemistry. Oxidase represents the enzymes that oxidize PACA to o-quinone, Protein-SH represents the protein bearing free cysteine residues. (B) Procedure for the isolation of PACA-modified proteins. (C) Western blotting analysis of PACA-modified proteins. PC12 cells were treated with PACA (20 μM) for 6 h. The cellular proteins were isolated and treated with Azido-Biotin under Click chemistry conditions. Click chemistry products were incubated with Keap1 antibody and subsequently isolated by Protein A/G agarose beads. All protein fractions were resolved by SDS-PAGE and detected by streptavidin-HRP conjugate. CL, cell lysates of PACA-treated PC12 cells; CRP, Click chemistry products; NB, non-bound fraction; W1, washing fraction-1 with PBS; W2, washing fraction-2 with PBS; W3, washing fraction with PBS; E, elution by heating the beads in 2× Laemmli sample buffer at 95° C. for 5 minutes.
Figure 5:
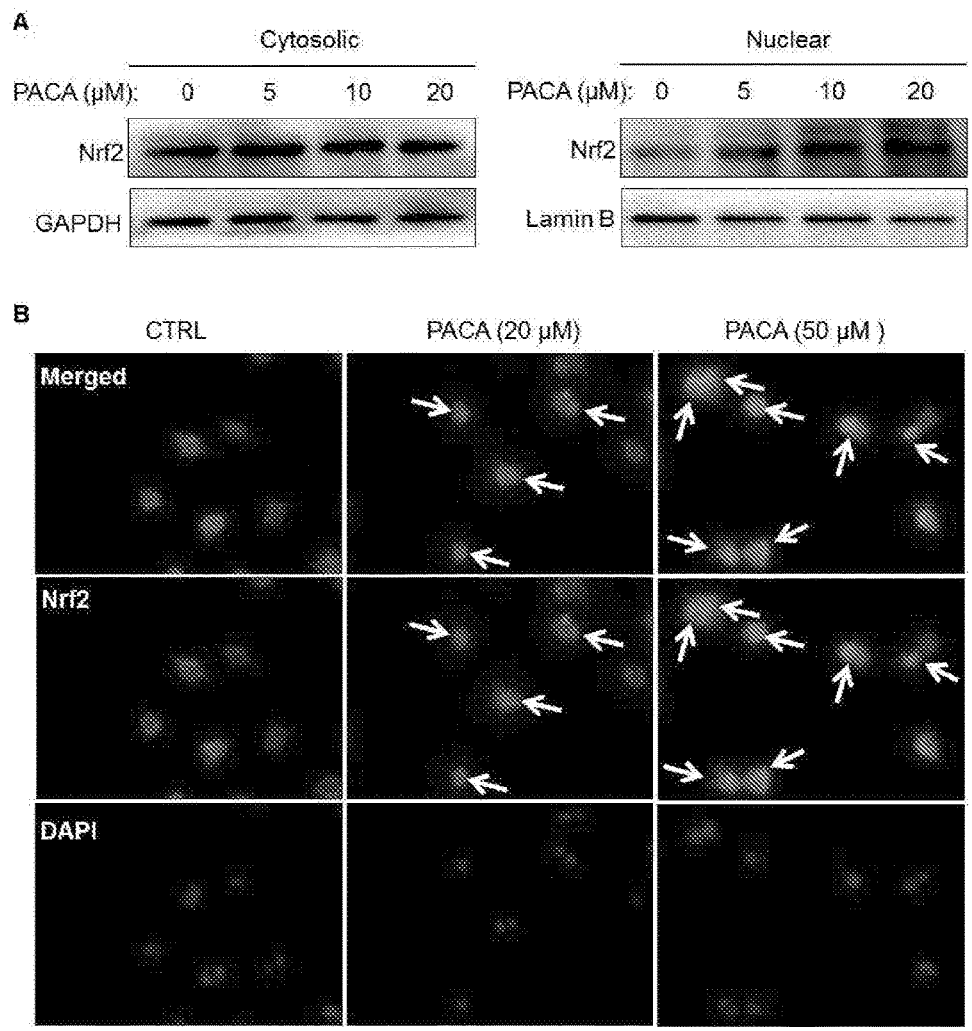
FIG. 5 shows PACA induced the translocation of Nrf2 into the cell nuclei. Direct modification of Keap1 caused the dissociation of Nrf2-Keap1 complex. Based on Western blot analysis of the nuclear proteins and immunostaining of intracellular Nrf2, PACA induced the translocation of Nrf2 into the cell nuclei in a concentration-dependent manner. (A) Western blot analysis of cytosolic and nuclear Nrf2. Following PACA treatment, the cytosolic and nuclear proteins were isolated and analyzed by Western blotting for Nrf2 expression. GAPDH and lamin b were analyzed as the control of protein loading. (B) Immunostaining of the intracellular Nrf2. Following PACA treatment, the cells were probed with Nrf2 antibody, and subsequently visualized with Alexa Fluor 586-conjugated secondary antibody. DAPI was used to detect the cell nuclei. The images were captured under a fluorescence microscope. The arrows point to the nuclear Nrf2.
Figure 6:
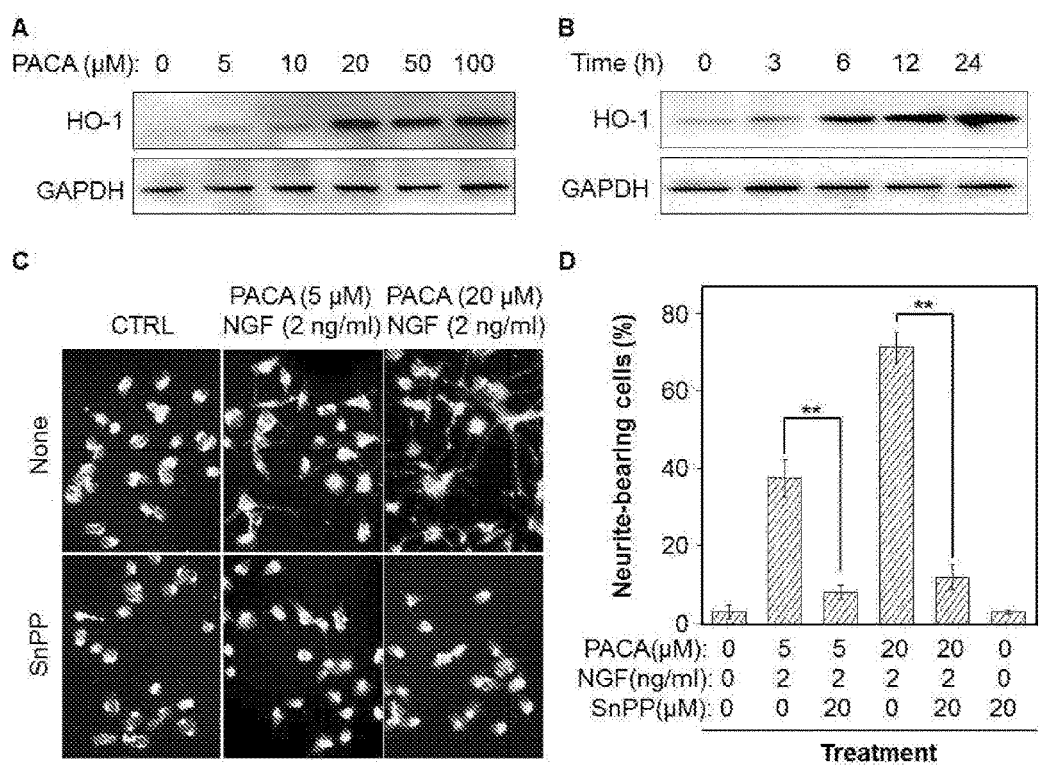
FIG. 6 shows PACA induced the expression of HO-1 and stimulated neurite outgrowth via HO-1-mediated mechanism. Following direct modification of Keap1, PACA sequentially induced the dissociation of the Nrf2-Keap1 complex and the expression of heme oxygenase-1 (HO-1) in a concentration- and time-dependent manner. Induction of HO-1 expression is a key mechanism underlying the neuritogenic effects of PACA. (A & B) Western blot analysis of HO-1 induction. Following PACA treatment at different concentrations (A) and for different time points (B), the cellular proteins were isolated and analyzed by Western blotting for HO-1 expression. GAPDH was analyzed as the control of protein loading. (C) PACA stimulated neurite outgrowth via HO-1-mediated mechanism. PC12 cells were treated with NGF (2 ng/ml) in combination with PACA (5 μM, 20 μM) in presence or absence of HO-1 inhibitor SnPP for 72 hours. Cells were stained by neurite outgrowth staining kit and imaged under a fluorescence microscope. (D) Role of HO-1 induction in the neuritogenic activity of PACA. The images captured in Panel C were analyzed for the number of neurite bearing cells. The cells bearing neurites longer than 20 μm were counted. The values represent means±SD (n=3). **, p<0.01 (+SnPP vs −SnPP).
Figure 7:
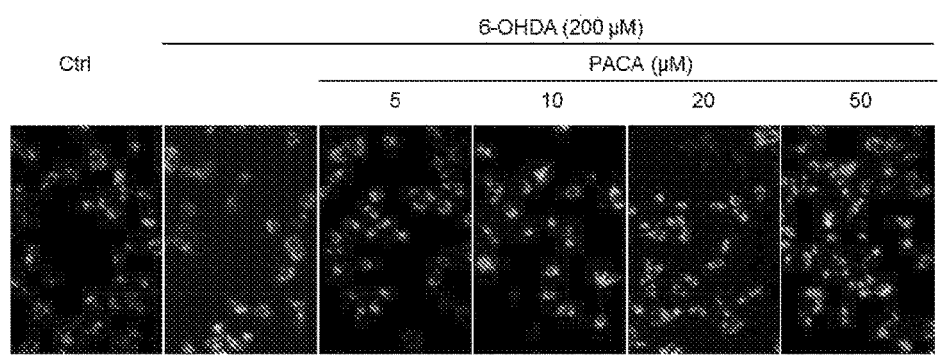
FIG. 7 shows PACA attenuated 6-OHDA-induced disruption of mitochondria member potential. By using fluorescent probe 5,5',6,6'-tetrachloro-1,1',3,3'-tetraethyl-benzimidazolcarbocyanine iodide (JC-1) to monitor the mitochondria member potential, PACA was found to suppress 6-OHDA-induced disruption of the mitochondria membrane integrity in a concentration-dependent manner. PC12 cells were treated with 6-OHDA alone or in combination with PACA for 6 hours and subsequently stained with JC-1. The images were captured under a fluorescence microscope.
Figure 8:
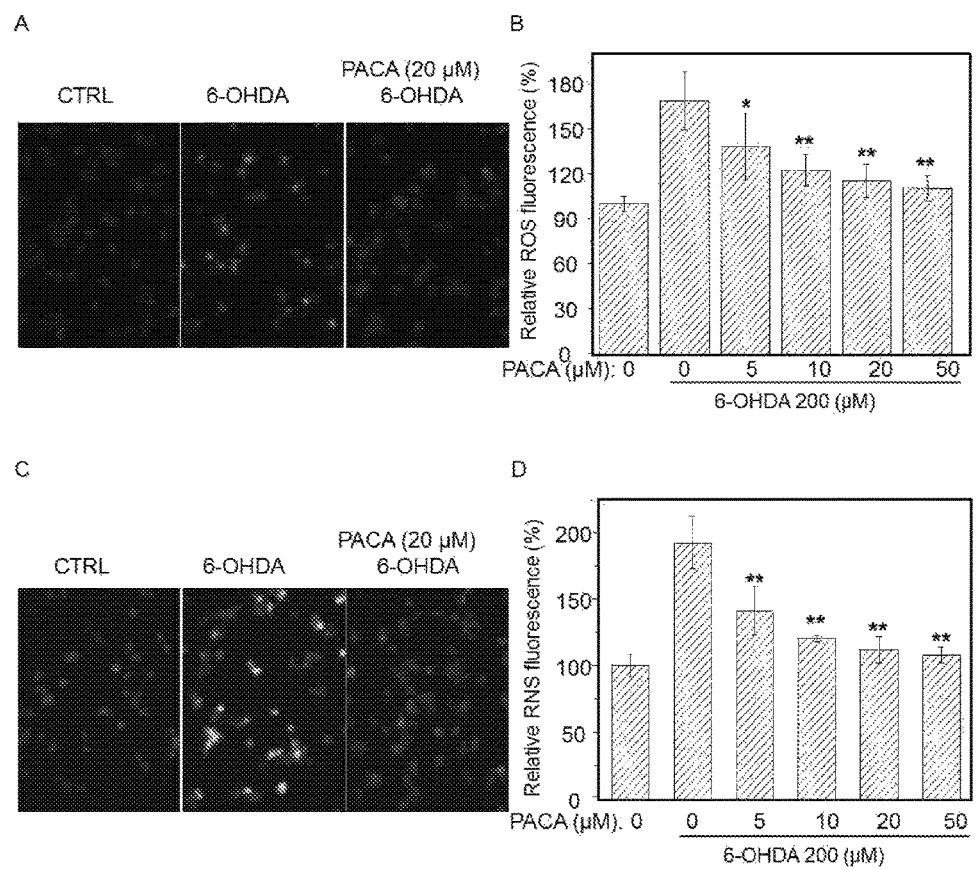
FIG. 8 shows PACA attenuated 6-OHDA-induced production of RNS and ROS. After the treatment with 6-OHDA alone or in combination with PACA at different concentrations, PC12 cells were stained with a fluorescent probe dihydroethidium (DHE) for the production of superoxide anion (A & B) and another fluorescent probe DAF-FM Diacetate for the production of nitric oxide (A & B), respectively. (A) Representative images of DHE-stained cells. 6-OHDA, 200 μM; PACA, 50 (B) PACA inhibited 6-OHDA-induced formation of superoxide ions. PC12 cells were treated with 6-OHDA alone or in combination with PACA for 6 h and subsequently stained with a probe DHE. The images were captured under a fluorescence microscope. The fluorescence was determined by ImageJ software. (C) Representative images of DAF-FM DA-stained cells. 6-OHDA, 200 μM; PACA, 50 μM. (D) PACA inhibited 6-OHDA-induced NO production. PC12 cells were treated with 6-OHDA alone or in combination with PACA for 6 h and subsequently stained with a probe DAF-FM DA. The images were captured under a fluorescence microscope. The fluorescence was determined by ImageJ software.
Figure 9:
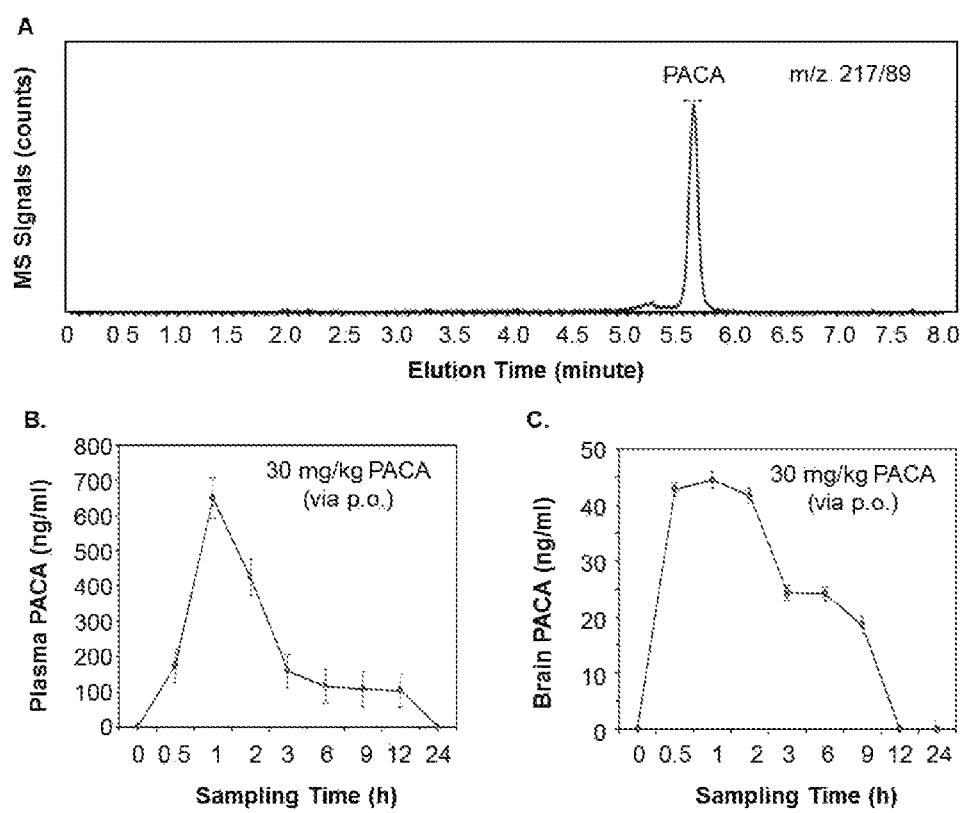
FIG. 9 shows pharmacokinetic analysis of PACA in mice. (A) HPLC-MS/MS detection of PACA. (B) Determination of PACA in mouse plasma. (C) Determination of PACA in mouse brain tissues. PACA (30 mg/kg) was orally administered into mice. Blood samples and brain tissues were collected after different times (0, 0.5, 1, 2, 3, 6, 9, 12 or 24 h). PACA was determined by liquid chromatography-mass spectrometric multiple reaction monitoring-based strategy.
Figure 10:
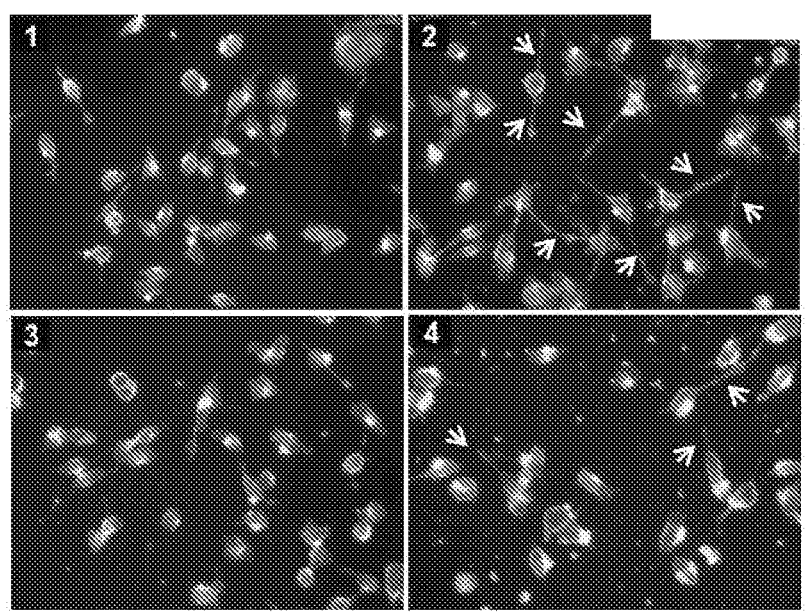
FIG. 10 shows fluorescence microscopy analysis showing unique neuritogenic activity of PACA. PC12 cells were treated with NGF (2 ng/ml) alone or in combination with PACA (20 μM), caffeic acid (20 μM) and CAPE (20 μM) for 72 h. Cells were stained by neurite outgrowth staining kit and imaged under a fluorescence microscope. Representative images of PC12 cells were shown while the white arrows were pointing to the neurites.
Figure 11:
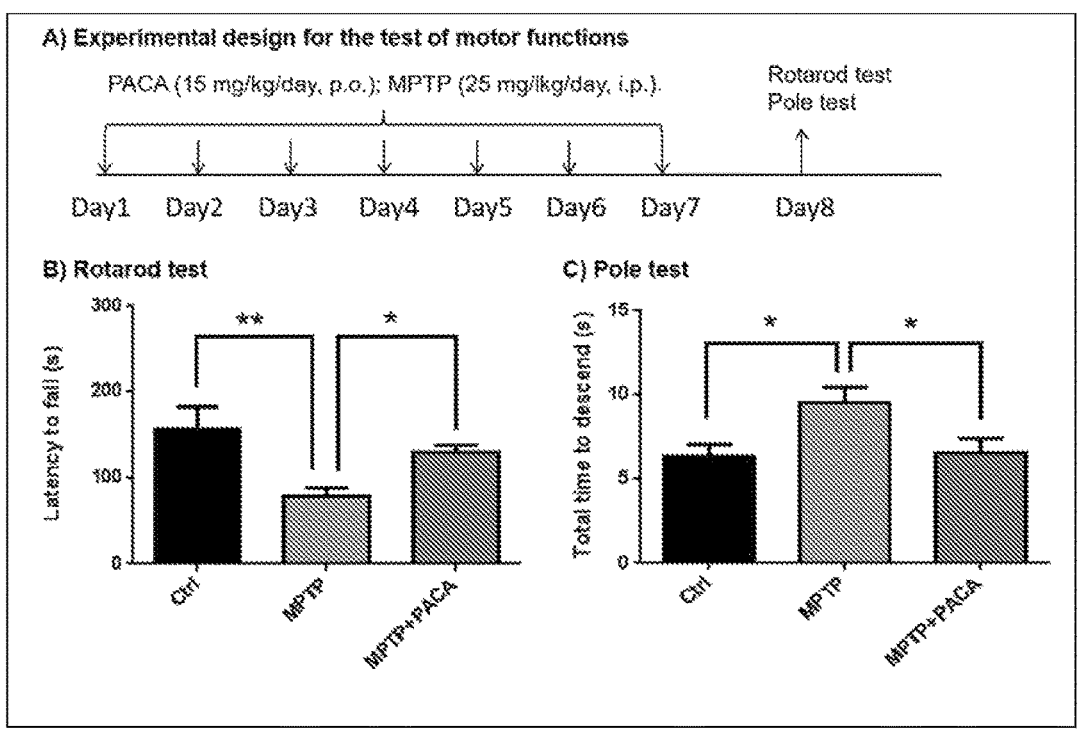
FIG. 11. In vivo Effect of PACA on MPTP-induced motor dysfunctions in mice. (A) Study design. (B) Rotarod test. Mice were placed on horizontal drums (30 mm in diameter), rotating at a progressively increasing speed, from 4 to 32 rpm over a 5-min period. The time that each animal stayed on the rod before falling was measured. (C) Pole test. Mice were placed with facing head-up on the top of the 50 cm long metal rod (1 cm diameter). Total time for each animal to reach the base of the pole was recorded. Each mouse was tested for three times. The data were presented as Mean±SEM and analyzed by one-way ANOVA with post-hoc Dunnett test. *$p<0.05$; **, $p<0.01$.

Insufficient production of neurotrophic factors is well-recognized in various neurodegenerative disorders. The present invention provides a synthetic method for the preparation of novel chemical N-propargyl caffeamide (PACA) and the use of this compound PACA as a novel neuroprotectant and neuritogenic agent for the treatment of neurodegenerative diseases, including Parkinson's disease. It was discovered that PACA not only potentiated NGF-induced neurite outgrowth but also attenuated 6-hydroxydopamine (6-OHDA) neurotoxicity in dopaminergic PC12 cells and primary rat midbrain neurons. To identify the PACA-binding proteins, a biotin tag was introduced to the covalent PACA-protein adducts via "Click chemistry" alkyne-azido cycloaddition. As a result, kelch-like ECH-associated protein 1 (Keap1) was isolated as the predominant protein from PACA treated PC12 cells. It was demonstrated that the formation of PACA-Keap1 conjugates induced the nuclear translocation of transcription factor Nrf2 and the expression of antioxidant heme oxygenase-1 (HO-1). Importantly, specific HO-1 inhibitor SnPP diminished the neuroprotective and neuritogenic activities of PACA. Moreover, PACA attenuated 6-OHDA-induced production of neurotoxic reactive oxygen species and reactive nitrogen species. PACA also preserved mitochondrial membrane integrity and enhanced the cellular resistance against 6-OHDA neurotoxicity. These results suggest that PACA exhibits neuroprotective and neuritogenic activities via activating the Nrf2/HO-1 antioxidant pathway.

Aspects of the present invention provide a compound of formula (1):

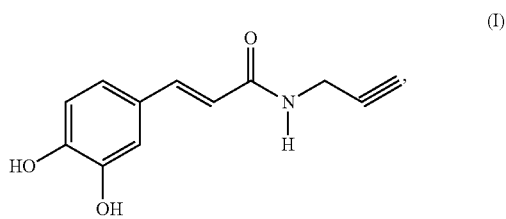 [SMILES: C#CCNC(=O)/C=C/c1ccc(O)c(O)c1]

which has the chemical name, N-propargyl caffeamide (PACA).

Aspects of the present invention also provide pharmaceutical compositions comprising the compound of formula (I) and a pharmaceutically acceptable carrier.

The term "pharmaceutically acceptable," as used herein with regard to pharmaceutical compositions, means approved by a regulatory agency of the Federal or a state government or listed in the U.S. Pharmacopeia or other generally recognized pharmacopeia for use in animals and/or in humans.

The term "carrier" refers to a diluent, adjuvant, excipient, and/or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients include starch, glucose, sucrose, gelatin, lactose, malt, rice, flour, chalk, silica gel, sodium stearate, glycerol monostearate, talc, sodium chloride, glycerol, propylene, glycol, water, ethanol and the like. The pharmaceutical composition may also contain wetting or emulsifying agents or suspending/diluting agents, or pH buffering agents, or agents for modifying or maintaining the rate of release of the compounds. These compositions can take the form of solutions, suspensions, emulsion, tablets, pills, capsules, powders, sustained-release formulations and the like. Oral formulations can include standard carriers such as pharmaceutical grades of mannitol, lactose, sodium saccharine, starch, magnesium stearate, cellulose, magnesium carbonate, etc. Such compositions will contain a therapeutically effective amount of the compound together with a suitable amount of carrier so as to provide the proper form to the patient based on the mode of administration to be used.

If for intravenous administration, the compositions are packaged in solutions of sterile isotonic aqueous buffer. Where necessary, the composition may also include a solubilizing agent. The components of the composition are supplied either separately or mixed together in unit dosage form, for example, as a dry lyophilized powder or concentrated solution in a hermetically sealed container such as an ampoule or sachette indicating the amount of active agent. If the composition is to be administered by infusion, it can be dispensed with an infusion bottle containing sterile pharmaceutical grade water or saline. Where the composition is administered by injection, an ampoule of sterile water or saline can be provided so that the ingredients may be mixed prior to injection.

Moreover, if a packaging material is utilized to package the pharmaceutical composition, it may be biologically inert or lack bioactivity, such as plastic polymers, silicone, etc. and may be processed internally by the subject without affecting the effectiveness of the compound packaged and/or delivered therewith.

Aspects of the present invention also provide methods of treating or preventing a neurodegenerative diseases in a subject, comprising administering an effective amount of the compound of formula (I) (i.e., PACA) to a subject in need thereof. In some embodiments, the neurodegenerative disease is Parkinson's disease. In some embodiments, PACA induces the nuclear translocation of Nrf2 and subsequent HO-1 induction via direct modification of Keap1. In some embodiments, PACA potentiates NGF-induced neurite outgrowth in HO-1 dependent manner. In some embodiments, PACA attenuates 6-OHDA induced neuron injury in HO-1 dependent manner. PACA is rapidly bioavailable in plasma and brain tissues after oral administration.

As used herein, "treatment" or "treating" refers to arresting or inhibiting, or attempting to arrest or inhibit, the development or progression of a disease and/or causing, or attempting to cause, the reduction, suppression, regression, or remission of a disease and/or a symptom thereof. As would be understood by those skilled in the art, various clinical and scientific methodologies and assays may be used to assess the development or progression of a disease, and similarly, various clinical and scientific methodologies and assays may be used to assess the reduction, regression, or remission of a disease or its symptoms. "Treatment" refers to both therapeutic treatment and prophylactic or preventative measures. Those in need of treatment include those already with the disease as well as those prone to have the disease or those in whom the disease is to be prevented. In at least one embodiment, the disease being treated or prevented is a neurodegenerative disease. In some embodiments, the disease being treated or prevented is Parkinson's disease.

Administration may be locally (confined to a single cell or tissue) and/or systemically in the subject. It may be desirable to administer the compounds and pharmaceutical compositions of the invention locally to the area in need of treatment, such as in the brain. This method of administration may be achieved by, for example, and not by way of limitation, local infusion during surgery, topical application (e.g., in conjunction with a wound dressing after surgery), by injection, by catheter, or by means of an implant (e.g., a porous membrane).

In some embodiments, the compounds or pharmaceutical composition can be delivered in a controlled release system. Such methods may include the use of a pump for administration (e.g., use of an intravenous drip). In another embodiment, a controlled release system can be placed in the proximity of the therapeutic target, requiring only a fraction of the dose required if dosed systemically.

Furthermore, it would be understood by those skilled in the art that the therapeutic methods described would not only apply to treatment in a subject, but could be applied to cell cultures, organs, tissues, or individual cells in vivo, ex vivo or in vitro.

It would also be understood by a skilled artisan how to use the compounds and/or pharmaceutical compositions of the present invention for diagnostic or therapeutic purposes without undue experimentation based on the teachings provided throughout the specification.

As used herein, the term "subject" refers to an animal. Typically, the terms "subject" and "patient" may be used interchangeably herein in reference to a subject. As such, a "subject" includes a human that is being treated for a neurodegenerative disease as a patient.

The term "animal," includes, but is not limited to, mouse, rat, dog, cat, rabbit, pig, monkey, chimpanzee, and human.

The terms "effective amount" and "therapeutically effective amount," used interchangeably, as applied to the compounds and pharmaceutical compositions described herein, mean the quantity necessary to render the desired therapeutic result. For example, an effective amount is a level effective to treat, cure, or alleviate the symptoms of the neurodegenerative disease for which the composition and/or pharmaceutical composition, is/are being administered. Amounts effective for the particular therapeutic goal sought will depend upon a variety of factors including the disease being treated and its severity and/or stage of development/progression; the bioavailability and activity of the specific compound or pharmaceutical composition, used; the route or method of administration and introduction site on the subject; the rate of clearance of the specific composition and other pharmacokinetic properties; the duration of treatment; inoculation regimen; drugs used in combination or coincident with the specific composition; the age, body weight, sex, diet, physiology and general health of the subject being treated; and like factors well known to one of skill in the relevant scientific art. Some variation in dosage will necessarily occur depending upon the condition of the subject being treated, and the physician or other individual administering treatment will, in any event, determine the appropriate dosage for an individual patient.

Aspects of the present invention also provide methods of stimulating neurite outgrowth in an area where neurite outgrowth is desired, the methods comprising administering an effective amount of a compound of formula (I) to cells in the area where neurite outgrowth is desired, whereby neurite outgrowth is stimulated. In some embodiments, the methods further comprise administering an effective amount of a nerve growth factor. The compound of formula (I) may stimulate neurite outgrowth in a heme oxygenase-1 dependent manner.

Aspects of the present invention also provide methods of attenuating neuron injury, comprising contacting neurons, in need thereof, with an effective amount of a compound of formula (I), whereby neuron injury is attenuated in a heme oxygenase-1 dependent manner.

Aspects of the present invention also provide methods of synthesizing PACA comprising the steps described in Example 1 and illustrated in FIG. 1.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Anyone or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By citation of various references in this document, Applicants do not admit any particular reference is "prior art" to their invention.

EXAMPLES

The methods, compounds, and compositions herein described are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented. All parts or amounts, unless otherwise specified, are by weight.

Example 1: Synthesis and Chemical Characterization of PACA

PACA was synthesized from caffeic acid and propargylamine through four steps, including acetylation, activation of carboxylic acid group, amination and deacetylation. In practical, caffeic acid (0.5 g) was acetylated by acetic anhydride (1 mL) in anhydrous pyridine (2 mL) at room temperature overnight to yield di-O-Ac-caffeic acid (579 mg, ~90%). Di-O-Ac-caffeic acid was converted into di-O-Ac-caffeic acid N-hydroxysuccinimide ester via reacting with N, N'-disuccinimidyl carbonate (1.28 g) in N, N-dimethylformamide (2 mL). Following the removal of solvents by rotatory evaporation under reduced pressure, the residues containing di-O-Ac-caffeic acid N-hydroxysuccinimide ester were treated with propargylamine (320 µL, 275 mg) at room temperature for 8 hours. The reaction mixture was treated with 3 equivalent NaOMe/MeOH for 2 hours. After the reaction was completed according to TLC detection, the reaction mixture was purified by gel chromatography on a silica column, yielding PACA, light yellow power, 325 mg, 60%. PACA was further characterized by mass spectroscopy (MS) and nuclear magnetic resonance (NMR) spectroscopy. MS analysis was performed on an ABI/Sciex triple quadrupole 3200 QTRAP mass spectrometer (Framingham, Mass., USA) equipped with a TurboV Source operating in positive ionization mode under the control of Analyst v1.4.2 data system (Applied Biosystems/MDS Sciex, Concord, ON, Canada). ESI-MS (m/z): 218 $[M+H]^+$, 435 $[2M+H]^+$. NMR spectra were recorded in MeOD: $CDCl_3$ (50:50, v/v) on a Varian Unity plus NMR 400 MHz spectrometer (Varian Inc., Palo Alto, Calif., USA). $^1H$ NMR (MeOD: $CDCl_3$, 400 MHz), $\delta_H$: 2.79 (1H, t, 2.4 Hz, H-3''), 4.50 (2H, d, 2.4 Hz, $H_2$-1''), 6.74 (1H, d, 15 Hz, H-2), 7.21 (1H, d, 8.1 Hz, H-6'), 7.33 (1H, d, 8.1 Hz, H-5'), 7.48 (1H, s, H-2'), 7.86 (1H, d, 15 Hz, H-3), 8.33 (1H, s, H—N); $^{13}C$ NMR (MeOD: $CDCl_3$, 75 MHz), $\delta_C$: 28.5 (C-3''), 70.9 (C-1''), 79.11 (C-2''), 113.7 (C-2'), 115.1 (C-5'), 116.4 (C-2), 121.3 (C-6'), 126.6 (C-1'), 141.5 (C-3), 144.5 (C-3'), 146.7 (C-4'), 167.3 (C-1).

Example 2: Neuritogenic Effect of PACA

The neuritogenic activity of PACA was evaluated in rat dopaminergic PC12 cells. PC12 cells were treated with NGF (2 ng/mL) alone or in combination with PACA at the concentrations of 5, 10, 20 µM for 72 hours. The cells were stained by a neurite outgrowth kit, and subsequently analyzed for neurites (>20 µm) under a fluorescence microscope. Compared with NGF alone, PACA significantly potentiated NGF-induced neurite outgrowth in a concentration-dependent manner. PACA (20 µM) alone did not induce neurite outgrowth. Interestingly, PACA (20 µM) and NGF (2 ng/mL) in combination increased the number of neurite-bearing cells by approximate 6-fold relative to NGF alone. Following the treatment with PACA and NGF, alone or in combination, PC12 cells were analyzed by Western blotting for the expression of neuronal biomarkers (i.e., β3-tubulin, MAP2 and GAP-43). Based on the induction of neuronal markers including β3-tubulin, MAP2 and GAP-43, PACA enhanced the neuritogenic activity of NGF in a concentration-dependent manner.

Example 3: Neuroprotective Effect of PACA

Neurotoxin 6-hydroxydopamine (6-OHDA) is widely used to induce the cell model of human Parkinsonism. PC12 cells were treated with 6-OHDA with or without PACA for 24-hours, the cell viability was assessed by the colorimetric MTT assay. The relative cell viability was plotted against the concentrations of PACA. On the other hand, primary midbrain neurons were isolated from 17-day-old Sprague Dawley (SD) rat embryos. The midbrain neurons were treated with 6-OHDA with or without PACA for 12-hours, the cell viability was assessed by the colorimetric MTT assay. Alternatively, the neurons were stained with 5 µM of Hoechst 33342 and 1 µM of PI in the differentiation medium at 37° C. for 30 minutes. The images were captured on a Zeiss fluorescence microscope.

Example 4: Identification of Keap1 as a Specific PACA-Modified Protein

PACA is converted to the chemically reactive o-quinone intermediate by the intracellular oxidases after PACA got inside the cells. The o-Quinone intermediate directly modifies the proteins bearing free cysteine residues. In practical, PC12 cells were treated with 20 µM PACA for 24 h. The cellular proteins were extracted from the PACA-treated cells. A biotin tag was introduced into PACA-modified proteins through a "Click" alkyne-azido cycloaddition for versatile affinity purification[27]. Biotinylated proteins were initially isolated by Streptavidin-agarose beads from Sigma-Aldrich (St Louis, Mo., USA). Following gel electrophoresis and Western blotting onto PVDF (polyvinylidene difluoride) membranes, HRP-streptavidin conjugate detected a predominant ~70 kDa protein band (data not shown). Such protein band was also detected by keap1 antibody through a similar procedure. To directly isolate PACA-modified Keap1 from cell culture system, biotinylated proteins were therefore pulled down by Keap1 antibody and Protein A/G beads. All protein fractions were resolved by gel electrophoresis and Western blotting onto PVDF membranes. The blots were probed by HRP-conjugated streptavidin, and subsequently detected by chemiluminescence. The 70 kDa protein band was predominantly captured by Keap1 antibody.

Example 5: PACA Induced the Translocation of Nrf2 into the Cell Nuclei

Direct modification of Keap1 caused the dissociation of Nrf2-Keap1 complex. Following the treatment with PACA at different concentrations, the intracellular localization of Nrf2 was examined by Western blotting and immunostaining methods. For Western blot analysis, the cellular proteins were separated into the cytosolic and nuclear fractions, and analyzed by Western blotting with Nrf2 antibodies. GAPDH was used as the control of protein loading, whereas Lamin B was detected as the nuclear biomarker. The results demonstrated that PACA significantly increased the levels of nuclear Nrf2 in a concentration-dependent manner. For immunostaining of the intracellular Nrf2, on the other hand, PC12 cells were sequentially probed with rabbit anti-Nrf2 antibody and detected by Alexa Fluor 594-conjugated goat anti-rabbit IgG antibodies PACA. The images were captured under a Zeiss fluorescence microscope. The results again confirmed that PACA promoted the accumulation of Nrf2 in the cell nucleus.

Example 6: PACA Induced HO-1 Expression and Subsequently Promoted Neurite Outgrowth in PC12 Cells It is well-known that direct modification of Keap1 causes the dissociation of the Nrf2-Keap1 complex and subsequent expression of heme oxygenase-1 (HO-1). Following the treatment with PACA at the concentrations ranging from 5 to 100 μM for 24 hours or at the concentration of 20 μM for 3, 6, 12, 24 hours, PC12 cells were analyzed by Western blotting for HO-1 induction. Based on Western blotting results, PACA indeed induced HO-1 expression in a time- and concentration-dependent manner.

To clarify the neuritogenic role of HO-1 induction, PC12 cells were treated with NGF, PACA and HO-1 inhibitor SnPP, alone or in combination, for 72 hours. The neurites were visualized by neurite outgrowth staining kit, and imaged under a fluorescence microscope. By using NIH ImageJ software, the number of neurite-bearing cells was compared in each treatment. As a result, HO-1 inhibitor SnPP significantly diminished the potential of PACA in the potentiation of NGF-induced neurite outgrowth.

Example 7: PACA Preserved the Mitochondria Membrane Integrity Against 6-OHDA-Induced Damage To investigate the neuroprotective mechanisms of PACA, PC12 cells were treated with 6-OHDA alone or in combination with PACA at the concentrations of 5, 10, 20 and 50 μM. At the end of treatment, the protection of PACA on the mitochondrial membrane integrity was examined by using a cell permeable fluorescent probe 5,5',6,6'-tetrachloro-1,1',3,3'-tetraethyl-benzimidazol-carbocyanine iodide (JC-1). 6-OHDA deadly disrupted the mitochondrial membrane integrity as indicated by the leakage of JC-1 into the cytosol. Interestingly, PACA well maintained MMP against 6-OHDA-induced membrane disruption and subsequent leakage of probe JC-1. The results suggested that PACA maintained the mitochondrial membrane integrity in a concentration-dependent manner.

Example 8: PACA Inhibited 6-OHDA-Induced Production of RNS and ROS

PC12 cells were treated with 6-OHDA alone or in combination with PACA at the concentrations of 5, 10, 20 and 50 μM. At the end of treatment, PC12 cells were then stained with a fluorescent probe dihydroethidium (DHE) for the production of superoxide anion and another fluorescent probe DAF-FM Diacetate for the production of nitric oxide, respectively. It was found that PACA significantly attenuated 6-OHDA-induced formation of not only superoxide ions but also neurotoxic NO in a concentration-dependent manner.

Example 9: Pharmacokinetic Analysis of PACA in Mice

Nine male Sprague Dawley rats with a body weight of 240-280 g were purchased from Laboratory Animal Unit, HKU. The animals were housed in a qualified facility run on a 12-hour light and dark cycle. The animals were allowed unrestricted access to food and water. The protocol for the animal studies was approved by Li Ka Shing Faculty of Medicine, University of Hong Kong. The rats were administered with PACA (30 mg/kg) in 50% propanediol in saline by oral gavage whereas the control animal received vehicle only. The rats were anesthetized by isoflurane at the time points of 0, 0.5, 1, 2, 3, 6, 9, 12 or 24 h. Blood samples were collected by cardiac puncture using pre-heparinized syringes and immediately transferred into the tubes containing acetonitrile for preventing esterase metabolism. Blood samples were centrifuged at 5700 rpm for 10 minutes at 4° C. to recover plasma. Brain tissues were excised after the removal of blood vessels, blotted dry with clean paper towels, and weighed. All samples were stored at −80° C. before use. HPLC separation was performed on a Phenomenex Synergi hydro-RP C18 reversed phase column (150 mm×4.6 mm, 4 m) (Torrance, Calif., USA) under the control of Agilent HLPC 1100 system (Santa Clara, Calif., USA). Gradient was set using mobile phase: A, water with 0.05% (v/v) formic acid, B, acetonitrile with 0.05% (v/v) formic acid as follows: 0-2.5 min, 40-50% B; 2.5-5.5 min, 50-80% B; 5.5-11.5 min, 80% B; 11.5-12 min, 80-40% B, 12-15 min, 40% B. Flow rate was constant at 0.7 mL/min. The column temperature was maintained at 30° C. Sample volume for injection was 20 μL. An ABI/Sciex Triple quadrupole mass spectrometer 3200 QTRAP® LC/MS/MS system (Applied Biosystems/MDS Sciex, Concord, ON, Canada) equipped with an ESI-Turbo V source operating in negative ionization mode was used for analysis. The system was controlled by Analyst v1.4.2 data system (Applied Biosystems/MDS Sciex, Concord, ON, Canada). MS analysis was conducted in electrospray positive mode. The mass spectrometer was operated with an ion spray voltage of −4.5 kV with 325° C. drying gas, 40 psi nebulizer gas and 60 psi turbo gas. Multiple-reaction monitoring (MRM) detection was used for the quantitation of all analytes.

Example 10: Unique Structural Element of PACA for Neuritogenic Activity

PC12 cells were treated with NGF (2 ng/mL) alone or in combinations with PACA (20 μM), caffeic acid (20 μM) and caffeic acid phenethyl ester (CAPE) (20 μM) for 72 hours. The cells were stained by neurite outgrowth staining kit. The images were captured on a Zeiss fluorescence microscope. Representative images of PC12 cells were shown while the white arrows were pointing to the neurites.

Example 11: In Vivo Neuroprotective Effect of PACA Against MPTP-Induced Motor Dysfunctions in Mice The in vivo neuroprotective effect of PACA was evaluated in a mouse model of Parkinson's disease. Nineteen mice were randomly divided into three groups: control (n=5), receiving vehicle administrations; MPTP (n=7), receiving i.p. injection of MPTP (25 mg/kg) every afternoon for seven days; MPTP+PACA (n=7), receiving p.o administration of PACA (15 mg/kg) every morning and i.p. injection of MPTP (25 mg/kg) every afternoon for seven days. At day-8, the motor functions of mice were assessed by rotarod performance test and pole test. The results suggested that PACA effectively protected animals against MPTP-induced motor dysfunctions.

Discussion

The present invention describes N-propargyl caffeamide (PACA), which is chemically derived from caffeic acid and propargylamine. PACA not only potentiated NGF-induced neurite outgrowth but also attenuated 6-hydroxydopamine (6-OHDA) neurotoxicity in rat dopaminergic PC12 cells and primary rat midbrain neurons. Mechanistic studies demonstrated that PACA activated the Nrf2/heme oxygenase-1 (HO-1) pathway via directly modifying Keap1. Consequently, PACA can attenuate 6-OHDA-induced production of neurotoxic reactive oxygen species and reactive nitrogen species. PACA can also preserve mitochondrial membrane integrity and enhance the cellular resistance against 6-OHDA neurotoxicity. After oral administration, PACA reaches the peak concentration in blood and brain tissues within 60 minutes. Thus, the use of PACA is taught as a neuroprotective and neurorestorative agent, and it can be used for the treatment of neurodegenerative diseases, including Parkinson's disease.

REFERENCES

1. Healy, D. G.; Falchi, M.; O'Sullivan, S. S.; Bonifati, V.; Durr, A.; Bressman, S.; Brice, A.; Aasly, J.; Zabetian, C. P.; Goldwurm, S.; Ferreira, J. J.; Tolosa, E.; Kay, D. M.; Klein, C.; Williams, D. R.; Marras, C.; Lang, A. E.; Wszolek, Z. K.; Berciano, J.; Schapira, A. H.; Lynch, T.; Bhatia, K. P.; Gasser, T.; Lees, A. J.; Wood, N. W.; International, L. C., Phenotype, genotype, and worldwide genetic penetrance of LRRK2-associated Parkinson's disease: a case-control study. *The Lancet. Neurology* 2008, 7, 583-90.
2. Perfeito, R.; Cunha-Oliveira, T.; Rego, A. C., Revisiting oxidative stress and mitochondrial dysfunction in the pathogenesis of Parkinson disease—resemblance to the effect of amphetamine drugs of abuse. *Free Radic Biol Med* 2012, 53, 1791-806.
3. Bonuccelli, U.; Del Dotto, P., New pharmacologic horizons in the treatment of Parkinson disease. *Neurology* 2006, 67, S30-8.
4. Muller, T., Non-dopaminergic drug treatment of Parkinson's disease. *Expert Opinion on Pharmacotherapy* 2001, 2, 557-72.
5. Meissner, W. G.; Frasier, M.; Gasser, T.; Goetz, C. G.; Lozano, A.; Piccini, P.; Obeso, J. A.; Rascol, O.; Schapira, A.; Voon, V.; Weiner, D. M.; Tison, F.; Bezard, E., Priorities in Parkinson's disease research. *Nature Reviews. Drug Discovery* 2011, 10, 377-93.
6. Marxreiter, F.; Regensburger, M.; Winkler, J., Adult neurogenesis in Parkinson's disease. *Cell Mol Life Sci* 2013, 70, 459-73.
7. Lamm, O.; Ganz, J.; Melamed, E.; Offen, D., Harnessing neurogenesis for the possible treatment of Parkinson's disease. *J Comp Neurol* 2014, 522, 2817-30.
8. Rangasamy, S. B.; Soderstrom, K.; Bakay, R. A.; Kordower, J. H., Neurotrophic factor therapy for Parkinson's disease. *Prog Brain Res* 2010, 184, 237-64.
9. Sullivan, A. M.; Toulouse, A., Neurotrophic factors for the treatment of Parkinson's disease. *Cytokine Growth Factor Rev* 2011, 22, 157-65.
10. Ma, Q., Role of nrf2 in oxidative stress and toxicity. *Annual Review of Pharmacology and Toxicology* 2013, 53, 401-26.
11. Joshi, G.; Johnson, J. A., The Nrf2-ARE pathway: a valuable therapeutic target for the treatment of neurodegenerative diseases. *Recent Patents on CNS Drug Discovery* 2012, 7, 218-29.
12. Satoh, T.; McKercher, S. R.; Lipton, S. A., Nrf2/ARE-mediated antioxidant actions of pro-electrophilic drugs. *Free Radic Biol Med* 2013, 65, 645-57.
13. Zhang, D. D.; Hannink, M., Distinct cysteine residues in Keap1 are required for Keap1-dependent ubiquitination of Nrf2 and for stabilization of Nrf2 by chemopreventive agents and oxidative stress. *Molecular and Cellular Biology* 2003, 23, 8137-51.
14. Paine, A.; Eiz-Vesper, B.; Blasczyk, R.; Immenschuh, S., Signaling to heme oxygenase-1 and its anti-inflammatory therapeutic potential. *Biochemical Pharmacology* 2010, 80, 1895-903.
15. Gozzelino, R.; Jeney, V.; Soares, M. P., Mechanisms of cell protection by heme oxygenase-1. *Annual Review of Pharmacology and Toxicology* 2010, 50, 323-54.
16. Karkkainen, V.; Pomeshchik, Y.; Savchenko, E.; Dhungana, H.; Kurronen, A.; Lehtonen, S.; Naumenko, N.; Tavi, P.; Levonen, A. L.; Yamamoto, M.; Malm, T.; Magga, J.; Kanninen, K. M.; Koistinaho, J., Nrf2 regulates neurogenesis and protects neural progenitor cells against Abeta toxicity. *Stem Cells* 2014, 32, 1904-16.
17. Zhao, F.; Wu, T.; Lau, A.; Jiang, T.; Huang, Z.; Wang, X. J.; Chen, W.; Wong, P. K.; Zhang, D. D., Nrf2 promotes neuronal cell differentiation. *Free Radic Biol Med* 2009, 47, 867-79.
18. Kumar, H.; Koppula, S.; Kim, I. S.; More, S. V.; Kim, B. W.; Choi, D. K., Nuclear factor erythroid 2-related factor 2 signaling in Parkinson disease: a promising multi therapeutic target against oxidative stress, neuroinflammation and cell death. *CNS & Neurological Disorders Drug Targets* 2012, 11, 1015-29.
19. Chen, L. W.; Wang, Y. Q.; Wei, L. C.; Shi, M.; Chan, Y. S., Chinese herbs and herbal extracts for neuroprotection of dopaminergic neurons and potential therapeutic treatment of Parkinson's disease. *CNS & Neurological Disorders Drug Targets* 2007, 6, 273-81.
20. Campos, H. C.; da Rocha, M. D.; Viegas, F. P.; Nicastro, P. C.; Fossaluzza, P. C.; Fraga, C. A.; Barreiro, E. J.; Viegas, C., Jr., The role of natural products in the discovery of new drug candidates for the treatment of neurodegenerative disorders I: Parkinson's disease. *CNS & Neurological Disorders Drug Targets* 2011, 10, 239-50.
21. da Cunha, F. M.; Duma, D.; Assreuy, J.; Buzzi, F. C.; Niero, R.; Campos, M. M.; Calixto, J. B., Caffeic acid derivatives: in vitro and in vivo anti-inflammatory properties. *Free Radical Research* 2004, 38, 1241-53.
22. Fiuza, S. M.; Gomes, C.; Teixeira, L. J.; Girao da Cruz, M. T.; Cordeiro, M. N.; Milhazes, N.; Borges, F.; Marques, M. P., Phenolic acid derivatives with potential anticancer properties—a structure-activity relationship study. Part 1: methyl, propyl and octyl esters of caffeic and gallic acids. *Bioorganic & Medicinal Chemistry* 2004, 12, 3581-9.
23. Yang, C.; Zhao, J.; Pei, W.; Zheng, X.; Rong, J., Biochemical mechanisms of bornyl caffeate induced cytotoxicity in rat pheochromocytoma PC12 cells. *Chem Biol Interact* 2014, 219C, 133-142.

24. Yang, C. B.; Pei, W. J.; Zhao, J.; Cheng, Y. Y.; Zheng, X. H.; Rong, J. H., Bornyl caffeate induces apoptosis in human breast cancer MCF-7 cells via the ROS- and JNK-mediated pathways. *Acta Pharmacologica Sinica* 2014, 35, 113-23.

25. Kurauchi, Y.; Hisatsune, A.; Isohama, Y.; Mishima, S.; Katsuki, H., Caffeic acid phenethyl ester protects nigral dopaminergic neurons via dual mechanisms involving haem oxygenase-1 and brain-derived neurotrophic factor. *Br J Pharmacol* 2012, 166, 1151-68.

26. Wei, X.; Zhao, L.; Ma, Z.; Holtzman, D. M.; Yan, C.; Dodel, R. C.; Hampel, H.; Oertel, W.; Farlow, M. R.; Du, Y., Caffeic acid phenethyl ester prevents neonatal hypoxic-ischaemic brain injury. *Brain* 2004, 127, 2629-35.

27. DeGuire, S. M.; Earl, D. C.; Du, Y.; Crews, B. A.; Jacobs, A. T.; Ustione, A.; Daniel, C.; Chong, K. M.; Marnett, L. J.; Piston, D. W.; Bachmann, B. O.; Sulikowski, G. A., Fluorescent probes of the apoptolidins and their utility in cellular localization studies. *Angew Chem Int Ed Engl.* 2015, 54, 961-4.

I claim:

1. A pharmaceutical composition comprising a pharmaceutically acceptable carrier and (E)-3-(3,4-dihydroxyphenyl)-N-(prop-2-yn-1-yl)acrylamide of the formula (I):

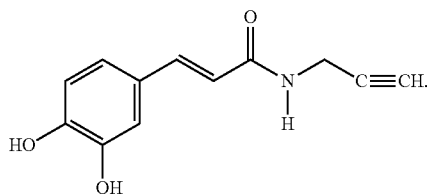

2. A method for stimulating neurite outgrowth in a subject in which neurite outgrowth is desired, the method comprising administering to the subject in need thereof a therapeutically effective amount of (E)-3-(3,4-dihydroxyphenyl)-N-(prop-2-yn-1-yl)acrylamide of the formula (I):

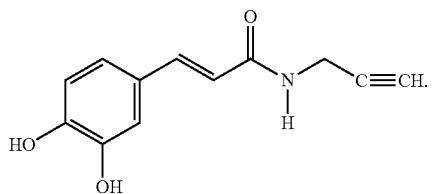

3. A method for stimulating neurite outgrowth in an area where neurite outgrowth is desired, the method comprising administering to cells in the area where neurite outgrowth is desired a therapeutically effective amount of (E)-3-(3,4-dihydroxyphenyl)-N-(prop-2-yn-1-yl)acrylamide of the formula (I):

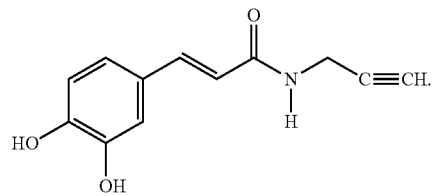

4. The method of claim 3, wherein the method further comprises administering to cells in the area where neurite outgrowth is desired a therapeutically effective amount of a nerve growth factor.

5. The method of claim 3, wherein the method further comprises (E)-3-(3,4-dihydroxyphenyl)-N-(prop-2-yn-1-yl) acrylamide stimulating neurite outgrowth via a heme oxygenase-1 dependent pathway.

6. A method for attenuating neuron injury in a subject, the method comprising administering to a subject having a neuron where neuron injury attenuation is desired a therapeutically effective amount of (E)-3-(3,4-dihydroxyphenyl)-N-(prop-2-yn-1-yl)acrylamide of the formula (I):

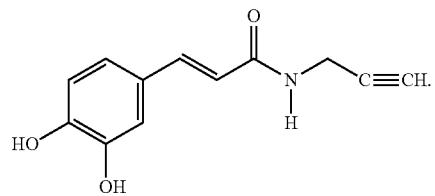

7. A method for attenuating neuron injury in a subject, the method comprising contacting a neuron in a subject in need thereof with a therapeutically effective amount of (E)-3-(3,4-dihydroxyphenyl)-N-(prop-2-yn-1-yl)acrylamide of the formula (I):

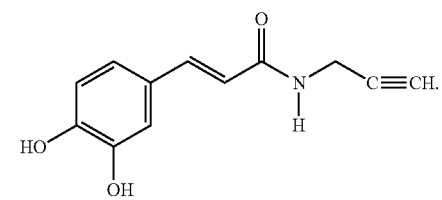

8. The method of claim 7, wherein the method further comprises attenuating neuron injury in the subject via a heme oxygenase-1 dependent pathway.

9. A process for preparing (E)-3-(3,4-dihydroxyphenyl)-N-(prop-2-yn-1-yl)acrylamide of the formula (I):

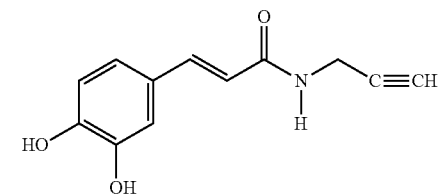

the process comprising the following steps:
(i) reacting (E)-3-(3,4-dihydroxyphenyl)acrylic acid of the formula:

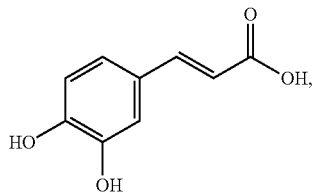

with acetic anhydride, to yield (E)-3-(3,4-diacetoxyphenyl)acrylic acid of the formula:

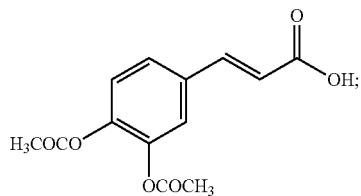

(ii) reacting (E)-3-(3,4-diacetoxyphenyl)acrylic acid of the formula above with N,N'-disuccinimidyl carbonate of the formula:

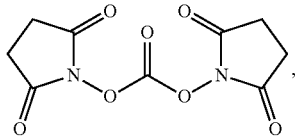 [SMILES: O=C(ON1C(=O)CCC1=O)ON1C(=O)CCC1=O]

to yield (E)-4-(3-((2,5-dioxopyrrolidin-1-yl)oxy)-3-oxoprop-1-en-1-yl)-1,2-phenylene diacetate of the formula:

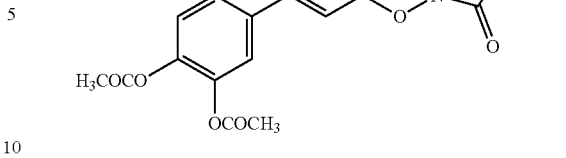

and (iii) reacting (E)-4-(3-((2,5-dioxopyrrolidin-1-yl)oxy)-3-oxoprop-1-en-1-yl)-1,2-phenylene diacetate of the formula above with propargylamine of the formula:

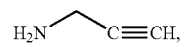

followed by sodium methoxide in methanol, to yield (E)-3-(3,4-dihydroxyphenyl)-N-(prop-2-yn-1-yl) acrylamide of the formula (I) above.

10. The method of claim 9, wherein the method further comprises reacting (E)-3-(3,4-dihydroxyphenyl)acrylic acid with acetic anhydride in the presence of anhydrous pyridine overnight at room temperature in step (i).

11. The method of claim 9, wherein the method further comprises reacting (E)-3-(3,4-diacetoxyphenyl)acrylic acid with N,N'-disuccinimidyl carbonate in the presence of N,N-dimethylformamide in step (ii).

12. The method of claim 9, wherein the method further comprises reacting (E)-4-(3-((2,5-dioxopyrrolidin-1-yl) oxy)-3-oxoprop-1-en-1-yl)-1,2-phenylene diacetate with propargylamine for 8 hours at room temperature in step (iii).

13. The method of claim 9, wherein the method further comprises isolating (E)-3-(3,4-dihydroxyphenyl)-N-(prop-2-yn-1-yl)acrylamide of the formula (I) by gel chromatography in step (iii).

14. The method of claim 13, wherein the gel chromatography is performed on a silica column.

* * * * *